United States Patent [19]

Wang

[11] Patent Number: 5,403,280

[45] Date of Patent: Apr. 4, 1995

[54] INFLATABLE PERFUSION CATHETER

[76] Inventor: James C. Wang, 15 Massasoit Ave., Norton, Mass. 02766

[21] Appl. No.: 191,219

[22] Filed: Feb. 2, 1994

Related U.S. Application Data

[63] Continuation-in-part of Ser. No. 17,763, Feb. 16, 1993, abandoned.

[51] Int. Cl.⁶ .............................................. A61M 29/00
[52] U.S. Cl. ..................................... 604/96; 604/101; 606/194
[58] Field of Search ................................. 604/96–103; 606/192–194

[56] References Cited

U.S. PATENT DOCUMENTS

| | | | |
|---|---|---|---|
| 4,141,364 | 2/1979 | Schultze | 604/96 |
| 4,183,102 | 1/1980 | Guiset | 604/101 |
| 5,254,089 | 10/1993 | Wang | 604/96 |
| 5,295,959 | 3/1994 | Gurbel et al. | 604/96 |
| 5,308,323 | 5/1994 | Sogawa et al. | 604/96 |

Primary Examiner—John D. Yasko
Assistant Examiner—Frank Wilkens, III

[57] ABSTRACT

A perfusion catheter for insertion into a body conduit, especially an artery. The catheter comprises a shaft (5) having at least one lumen (7) for delivery of a fluid inflation media and an array (1) formed of a plurality of radially disposed inflatable balloons (3) disposed in a cylindrical array around the shaft (5), each of the balloons (3) sharing a common wall (3a) with adjacent balloons (3). The balloons (3) are inflated by an array of channels (11) and separated from each other by a web (19). There is at least one opening (17) between two adjacent channels (11) to allow the flow of fluids into the array (1).

22 Claims, 3 Drawing Sheets

INFLATABLE PERFUSION CATHETER

RELATION TO OTHER APPLICATIONS

This application is a continuation in part of my application Ser. No. 08/017,763, filed Feb. 16, 1993, now abandoned.

BACKGROUND OF THE INVENTION

The present invention relates to catheters that can be placed in body conduits where there is a necessity to provide a continuous flow of body fluids past the catheter. The invention particularly relates to coronary dilation catheters for use in administering treatments to widen a constricted blood flow passage frequently caused by a stenosis in, for example, a heart valve or coronary artery.

A stenosis is a region of a blood vessel which has been narrowed to such a degree that blood flow is restricted. If the stenosis is severe, treatment is required to restore adequate blood flow and often such treatment requires surgery or angioplasty. Transluminal angioplasty is a procedure for treating a patient having a stenosis or constricted region in a coronary artery. Frequently the stenosis can be expanded so that the artery will permit an acceptable blood flow rate.

Coronary angioplasty includes the insertion of a balloon catheter through a patient's artery to the arterial stenosis and injecting a suitable fluid into the balloon to inflate it and hence expand the stenosis radially outwardly and compress it against the artery wall. Angioplasty has become a successful alternative to coronary arterial bypass surgery. The stenosis is compressed radially outward against the arterial wall to increase the cross-sectional area of the artery so that the artery has an acceptable blood flow rate.

Ordinary balloon catheters have a balloon fastened around the exterior of a hollow catheter tube. A tubular shaft is fastened to the balloon and the balloon is in fluid flow relation with the interior of the shaft. The shaft provides a fluid supply for inflating the balloon.

Coronary dilation catheters previously used in coronary angioplasty have the disadvantage of completely occluding the flow of blood while the balloon is expanded in the artery. However complete occlusion of a coronary artery cannot be permitted for any significant time without incurring serious risk of damage to portions of the heart that must receive blood from the occluded artery. Thus the balloon is pressurized for only a few seconds before it is depressurized to permit resumption of blood flow through the region of the stenosis. The inflation times currently used are limited and can range from 15 seconds to 3 minutes, depending on the patient being treated. The limited inflation time frequently is not sufficient to treat a stenosis and inflations must be repeated. Further, even if the arterial lumen is successfully dilated the effect may be only temporary. Restenosis of the artery after treatment is not uncommon. The sustained inflation of the balloon catheter, rather than short multiple inflations, reduces the possibility of post treatment restenosis and other clinical abnormalities.

DESCRIPTION OF THE PRIOR ART

Catheters have been devised which allow blood to flow by them while they are inflated. Such catheters are called balloon perfusion catheters. Commonly such perfusion catheters have a perfusion shaft with a plurality of openings which permit blood flow through the artery during balloon inflation. The openings generally spirally circumscribe the perfusion shaft both proximally and distally of the balloon, each opening being radially offset from adjacent openings. The blood thus flows into the perfusion shaft to exit on the other side of the balloon. Such a catheter is described in the U.S. Pat. No. to Horn et al, 5,087,247. Another example of perfusion catheters is disclosed in U.S. Pat. No. to Sabota, 4,581,017. The catheter described in Sabota involves the disposition of the several radially offset lobes which are individually inflatable by minor lumens that are disposed outside of the principle lumen. The blood passes by the lobes without entering a perfusion shaft. The pressure exerted against the stenosis is not uniformly distributed. Also the perfusion rate is somewhat limited especially when a long balloon is used. Generally, the tube through which the blood flows is small in size, 0.030 inches ID. It cannot be made larger since that would increase an already large profile (outer diameter) in the deflated balloon. When the defined profile of the deflated balloon is too large it cannot be used in tight lesions.

SUMMARY OF THE INVENTION

According to the present invention I have discovered an inflatable channeled perfusion catheter utilizing a cylindrical array of radially disposed, individually inflatable balloons for insertion into a body conduit. The perfusion catheter of the present invention avoids the necessity of passing body fluids through a lumen and then out to bypass the place where a balloon is lodged. Moreover when used to treat an arterial stenosis, the external sides of the array of balloons can exert a substantially uniform radial pressure on the artery wall. The cylindrical array of balloons is disposed around a hollow shaft, which in some cases may be removed after insertion of the catheter in the body conduit. At least one lumen is provided in the shaft to deliver fluid inflation media to the balloons. The balloons are individually inflatable through individual channels which are attached in a fluid flow relationship with the lumen in the shaft. The channels are separated from each other by webs. Upon inflation of the balloons, the balloons will spread apart and openings that are made in some of the webs will spread apart to provide for the flow of blood through them, into the array and out the other side of the catheter.

The catheter allows the body fluids to flow through the entire interior of the cylindrical array which enables the continuation of a high rate of body fluid flow. Adequate dilation for arterial work forces the balloons to engage the stenosis. Through changing dimensions and process variables in blowing (forming) of the balloon, the dilation force and the fluid flow rate can be balanced for optimum performance.

In the manufacture of the array of balloons, a hollow tube of two or more dissimilar plastics material is co-extruded using conventional extrusion techniques. A discrete phase, that is the phase which serves as the precursor of the channels (and which dictates their location and shape) is formed of high density polyethylene, Nylon, low density polyethylene or polyethylene copolymers. A continuous phase, that is the phase that will form the balloons with the discrete phase disposed therein, can be formed of polyethylene terephthalate or high or low density polyethylene. High density polyethylene, low density polyethylene and polyethylene copolymers can be extruded within polyethylene terephthalate. Nylon can be extruded within the high or low density polyethylene. After the phases are co-extruded, the discrete phase is withdrawn from the continuous phase to leave the channels inside the continuous phase. Co-extrusion of two plastics materials is well known and conventional techniques are used for such processes. The essential criteria for matching of two plastics materials is that they not adhere to each other after extrusion and that the discrete phase can be withdrawn from the continuous phase and leave channels therein.

While co-extrusion is preferred to form the balloons, it is also possible to extrude tubes with the channels already in them using known extrusion dies. Because the thickness of the precursors to the channels are so narrow, normally between about 0.025 and 0.5 mm. within a tube having a wall thickness between about 0.07 and 1.0 mm. and outside diameter between about 0.25 and 5.0 mm., I have found that extrusion with preformed channels is not always satisfactory and that co-extrusion is best.

The many other objects, features and advantages of the present invention will become apparent from the following description.

DESCRIPTION OF THE PREFERRED EMBODIMENTS

Figure 1:
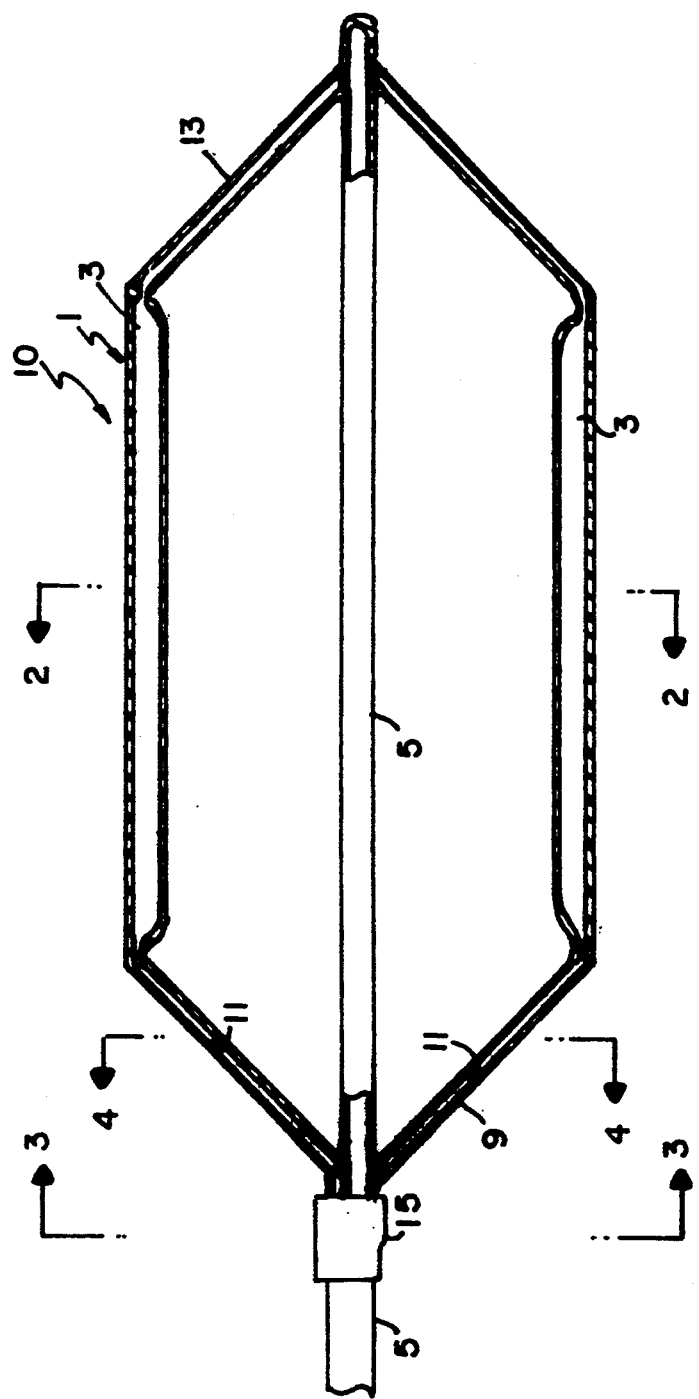
FIG. 1 is a cross-sectional view of a perfusion catheter in the inflated condition according to an embodiment of the present invention. The view is taken along the line 1—1 of FIG. 2.

Referring now to FIG. 1 the catheter 10 of the present invention includes an inflatable cylindrical array 1 of radially disposed balloons 3. Each of the balloons 3 in the array 1 are in fluid flow relation with an inflation lumen disposed in a shaft 5 as will be explained hereinafter. A hub 15 is disposed around the shaft 5 to secure the assembly. A proximal intermediate member 9 connects the hub 15 with the array of balloons 3. Channels 11 are formed in the proximal intermediate member 9 to provide fluid passageways between an inflation lumen 7 within the shaft 5 and the interiors of the balloons 3. Inflation lumen 7 may be one of several lumens in the shaft 5 as will be explained hereinafter.

The balloons 3 are also connected to a distal intermediate member 13. In the herein depicted embodiment the shaft 5 is disposed centrally within the array 1 to provide support for the array 1 by means of the distal intermediate member 13. In other embodiments, not shown, the shaft 5 is terminated at the hub 15 and the array 1 and the distal intermediate member 13 can be self supporting.

Inflation of the balloons 3 causes the array 1 to expand from a folded arrangement around the shaft 5 to being spaced therefrom to provide for an interior passageway for perfusion of fluids in the body conduit in which the catheter is disposed. The expansion also causes the proximal and distal intermediate members 9 and 13 to assume generally conical shapes and allow for the expansion of the array 1 against the lesion being addressed. In the collapsed state the profile of the balloons 3 can approximate the diameter of the shaft 5 because extremely thin walled balloons can be employed, as will be described hereinafter.

Figure 2:
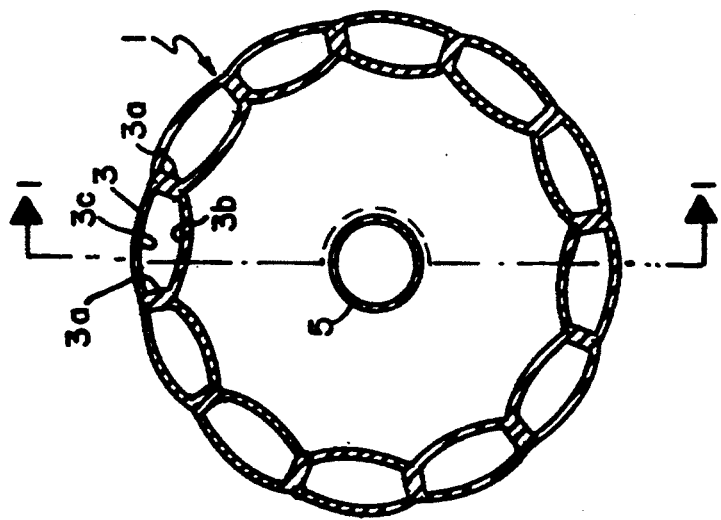
FIG. 2 is a cross-sectional view of the perfusion catheter shown in FIG. 1 taken along the line 2—2.

Referring now to FIG. 2, the balloons 3 are shown in an inflated state. Each of the balloons 3 have side walls 3a, an inner wall 3b and an outer wall 3c. The balloons 3 are disposed in a cylindrical array around an axis which can be the shaft 5. Each of the balloons 3 share a common side wall 3a with the next adjacent balloon 3 to enable the expansion of the balloons 3 into the cylindrical array 1 upon inflation. In FIG. 2 the proximal intermediate member 9 is not shown to provide for a simplified depiction of the invention. The wall thickness of each of the walls 3a, 3b and 3c can be between about 0.0001 and 0.004 in. with 0.0003 to 0.002 in. being preferred. The deflated profile of the array 1 can be 0.003 in. or less. The interior of the array, that is the space between oppositely disposed inflated inner walls 3b, can be between about 0.02 and 2.0 in. With such a wide passageway body fluids can flow substantially unimpeded from one end of the array to the other and out without significant interruption. Thus a high flow rate of fluids can be achieved while still maintaining an adequate dilation force against the body conduit being treated.

Figure 3:
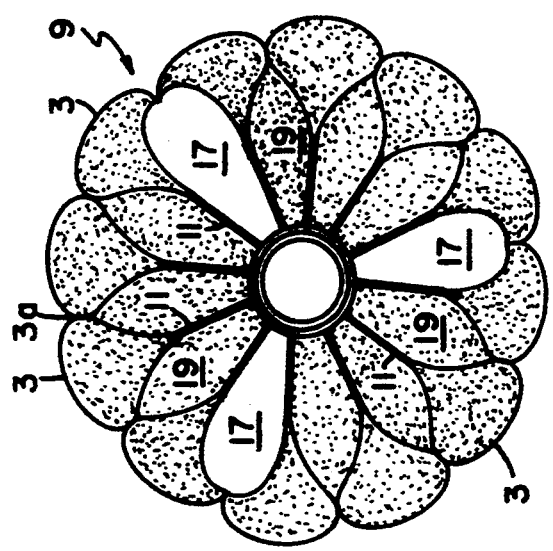
FIG. 3 is an end view of the perfusion catheter showing the relative dispositions of the array of balloons, webs and channels in the proximal end of the catheter. The view is taken along the line 3—3 of FIG. 1.
Figure 5:
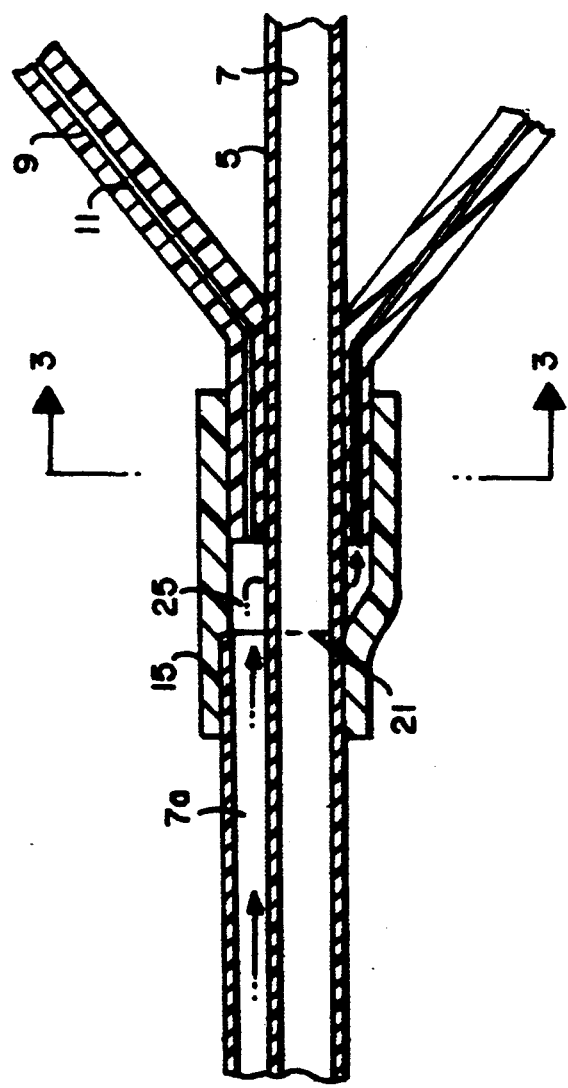
FIG. 5 is an enlarged cross-sectional view of the catheter showing particularly the fluid connection of the balloons to a lumen in the shaft.

Referring to FIG. 3 the proximal end of the catheter assembly, that is the proximal intermediate member 9, is shown. Each of the balloons 3 are arrayed cylindrically around the axis of the catheter. Each of the side walls 3a of the balloon 3 is an integral part of an adjacent side wall 3a of an adjacent balloon 3. Each of the balloons 3 is connected to a supply of inflation fluid by means of a channel 11 formed within the proximal intermediate member 9. The channels 11 are separated from each other by webs 19 which form integral parts of the proximal intermediate member 9. In one or more locations on the proximal intermediate member 9 a slit is made between adjacent channels 11 to form an opening 17 through which body fluids can flow beneath the inner wall 3b of the array of balloons (see FIG. 1). Each of the channels 11 in the proximal intermediate member 9 terminate in a central manifold area adjacent the proximal end of the catheter as shown in FIG. 5.

The distal intermediate member 13 can be a mirror image configuration of the proximal intermediate member 9, except that there is no need to carry inflation media within channels formed therein.

Figure 4:
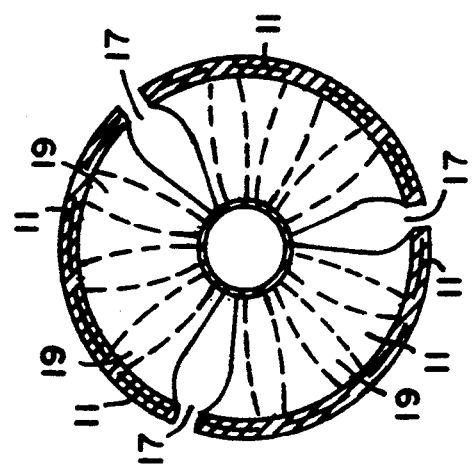
FIG. 4 is a cross-sectional interior view of the array of balloons taken along the line 4—4 of FIG. 1.

In FIG. 4, a cross-sectional view is shown of the interior of the proximal intermediate member 9. The channels 11 are shown as dotted lines within body of the webs 19 and as full lines within the cross-section. Each of the channels 11 are connected to the inflation lumen of the shaft 5 so that inflation media can be delivered to the balloons. Several openings 17 are cut within the proximal intermediate member 9 when the cylindrical array of balloons is inflated. Subsequent heating of the member 9 causes the edges of the cuts to shrink to adjacent the outsides of the channels 11 to widen the openings 17.

To make the channels within the proximal intermediate member 9, I have found that providing mild heating to the proximal intermediate member 9 while the channels 11 are filled with gas at about atmospheric pressure and while gas is also forced into the inflation lumen in shaft 5 causes dilation and stretching of the member 9. The operation enables cutting of slits in the web 17 between two adjacent channels 11. The pressure exerted by the inflation of the balloons 3 against the side walls 3a and the mild heat causes the channels 11 and the web 19 to spread apart and shrink the edges to widen the openings 17. The FIG. 4 illustrates the proximal intermediate member 9 and a mirror image construction and the configuration can be embodied in the distal intermediate member 13. The openings in the distal intermediate member 13 can be substantially identical to openings 17 in the proximal intermediate member 9. Of course there is no need for the channels 11 to carry inflation media in the distal intermediate member.

Referring now to FIG. 5 the joint between the proximal intermediate member 9 and the shaft 5 with the inflation lumen 7 is shown. Shaft 5 can be formed with a minor lumen 7a and the major lumen 7. The minor lumen 7a carries the inflation fluid to the channels 11 in the proximal intermediate member 9 (which in turn relays the fluid to the array of balloons). Lumen 7 can extend within the interior of the array to hold a guidewire that extends from the distal tip of shaft 5 (not shown, but as conventional in the art).

In a preferred embodiment, shaft 5 is formed with two segments, one terminating at the end of minor lumen 7a and being joined, without minor lumen 7a, to another shaft of similar dimensions at a joint 21. A hub 15 of shrinkable plastic is attached to both shaft 5 and the outside of the end of the proximal intermediate member 9. A manifold 25 is formed between the opening between the end of minor lumen 7a and the end of proximal intermediate member 9. Inflation fluid flowing from minor lumen 7a enters into the manifold 25 and thence to channels 11 and ultimately to balloons 3 (not shown) to inflate them. Sealing the sections of the shaft together and sealing the shaft to the hub 15 and to the end of the proximal intermediate member 9 is in accordance with conventional techniques used in the art for sealing such elements together.

In the manufacture of the herein described balloon assembly there is a requirement to create large openings near or on both ends of the balloon to enable the blood to flow from one end to the other without impeding its progress significantly. None of the channels can be blocked or cut through because in order to obtain adequate dilation force all of the channels must be inflated. Moreover, the openings should be made as close to the balloon as possible in order to reduce resistance to flow and it is essential that the openings be made as big as possible again to reduce flow resistance.

According to the present invention a tube is co-extruded with two or more dissimilar materials. Such materials have been described above. For example, one phase, a discrete phase, is formed of materials such as high density polyethylene. This phase can be drawn to form a tube with a plurality of channels in it. Co-extrusion of such materials is well known in the art and the shapes of the channels can be varied as desired by the operator.

The preferred method of manufacture of the balloons is then commenced by heating the tubing in the predetermined area where the balloons are to be formed and then simultaneously pressurizing both the channels and the areas of balloon formation and the interior of the balloon, that is the area adjacent inner walls 3b. The balloons will then expand to the desired diameter. After the balloons have been expanded, the proximal and distal intermediate members are formed by keeping each of these areas either simultaneously or sequentially inflated while not pressurizing the inside of the channels. In that way the balloons will expand but the spaces between the individual channels can be stretched and widened and one can safely cut the web between these channels to form the openings required for the flow of body fluids without severing the channels. A predetermined number of slits are made in the webs. The heating will cause the plastic to shrink and open the slits up to form big openings for the flow of fluids.

It is apparent that modifications and changes can be made within the spirit and scope of the present invention but it is my intention, however, only to be limited by the scope of the appended claims.

As my invention I claim:

1. A perfusion catheter for insertion into a body conduit, said catheter comprising:
   a shaft having at least one lumen for delivery of a fluid inflation media;
   an array formed of a plurality of radially disposed inflatable balloons having proximal ends, the balloons of said array being inflatable to form a generally cylindrically shape having inner and outer sides, said outer sides being arranged to engage a body conduit;
   means to inflate each of said balloons, said means including a plurality of channels, each channel being in fluid flow relationship with the proximal end of one of said balloons and said lumen;
   at least one opening between two adjacent channels to allow the flow of body fluids from the proximal ends, within said array and out the catheter.

2. The perfusion catheter according to claim 1 wherein said channels extend into the distal ends of each of the balloons and the channels are separated from each other by webs whereby to form a proximal intermediate member and said opening is in at least one of said webs.

3. The catheter according to claim 2 wherein the channels and the webs together form a proximal intermediate member.

4. The catheter according to claim 3 further including a distal intermediate member attached to said array, said distal intermediate member also having at least one opening in it.

5. The catheter according to claim 4 wherein said shaft extends through both said proximal and distal intermediate members.

6. The catheter according to claim 5 wherein said proximal intermediate member is joined to said shaft by a hub, said hub forming a manifold with a lumen in said shaft whereby fluid flow communication between said channels and said lumen is provided.

7. A perfusion catheter for insertion into a body conduit, said catheter comprising:
   a shaft having at least one lumen for delivery of a fluid inflation media;
   a cylindrical array of a plurality of radially disposed inflatable balloons having proximal and distal ends arranged around said shaft, each balloon sharing a common wall with an adjacent balloon, outer sides of said cylindrical array being arranged to engage said body conduit;

means to inflate each of said balloons, said means including a plurality of channels in fluid flow relationship with the proximal ends of said balloons, one end of each of said channels being connected to a common manifold in fluid flow with said lumen and the other end of each being connected to one of said balloons;

at least one opening between two adjacent channels to allow the flow of body fluids through, within and to the other side of said cylindrical array.

8. A perfusion catheter for insertion into a body conduit, said catheter comprising:

a shaft having at least one lumen for delivery of a fluid inflation media;

a cylindrical array of a plurality of radially disposed inflatable balloons having proximal and distal ends arranged around said shaft, each balloon sharing a common wall with an adjacent balloon, outer sides of said cylindrical array being adapted to engage said body conduit;

means to inflate each of said balloons, said means including a plurality of channels in fluid flow relation with the proximal ends of said balloons, said channels being separated from each other by a web, said webs being disposed between adjacent channels;

an opening in at least one of said webs between two adjacent channels to allow the flow of body fluids through and within and to the other side of said cylindrical array.

9. The catheter according to claim 8 wherein the channels and the webs together form a proximal intermediate member.

10. The catheter according to claim 9 further including a distal intermediate member attached to said array, said distal intermediate member also having at least one opening in it.

11. The catheter according to claim 10 wherein said shaft extends through both said proximal and distal intermediate members.

12. The catheter according to claim 11 wherein said proximal intermediate member is joined to said shaft by a hub, said hub forming a manifold with a lumen in said shaft whereby fluid flow communication between said channels and said lumen is provided.

13. A catheter which allows the passage of blood through a body conduit while an array attached thereto is inflated, said catheter comprising:

a shaft having an internal lumen for the introduction of an inflation fluid;

a radially expandable, inflatable cylindrical array of balloons disposed around said shaft, said array having an interior face and a body conduit engaging face;

means for connecting said array to said shaft for enabling the introduction of inflation media to the balloons of said array; and means for allowing the flow of body fluids between said shaft and said interior face whereby the flow of body fluids through said conduit will not be prevented when said array is inflated.

14. The catheter according to claim 13 wherein the means for connecting the shaft to the balloons to the shaft are a plurality of channels spaced from each other by webs.

15. The catheter according to claim 14 wherein the means for allowing the flow of body fluids is at least one opening in a web between adjacent channels.

16. A perfusion catheter for insertion into a body conduit, said catheter comprising:

a shaft having at least one lumen for delivery of a fluid inflation media;

a cylindrical shell of a plurality of radially disposed inflatable balloons having proximal and distal ends and an inner and outer side arranged around said shaft, the outer sides of said cylindrical shell being arranged to engage said body conduit;

means to inflate each of said balloons, said means including a plurality of channels in fluid flow relationship with the proximal ends of said balloons, said channels being separated from each other by a web, said web being disposed between adjacent channels;

a opening in at least one of said webs between adjacent channels to allow the flow of body fluids through and within and to the other side of said cylindrical array.

17. A perfusion catheter for insertion into a body conduit, said catheter comprising:

a shaft having at least one lumen for delivery of a fluid inflation media;

a cylindrical array of a plurality of radially disposed inflatable balloons having proximal and distal ends arranged around said shaft, each balloon sharing a common wall with an adjacent balloon, outer sides of said cylindrical array being adapted to engage said body conduit;

means to inflate each of said balloons, said means including a plurality of channels in fluid flow relationship with the proximal ends of said balloons, one end of each of said channels being connected to a common manifold and the other end of each being connected to the distal end of one of said balloons;

at least one opening between two adjacent channels to allow the flow of body fluids through and within and to the other side of said cylindrical array.

18. The perfusion catheter according to claim 17 wherein said channels are separated from each other by webs whereby to form a proximal intermediate member and said opening is in at least one of said webs.

19. The catheter according to claim 18 wherein the channels and the webs together form a proximal intermediate member.

20. The catheter according to claim 19 further including a distal intermediate member attached to said array, said distal intermediate member also having at least one opening in it.

21. The catheter according to claim 20 wherein said shaft extends through both said proximal and distal intermediate members.

22. The catheter according to claim 21 wherein said proximal intermediate member is joined to said shaft by a hub, said hub forming a manifold with a lumen in said shaft whereby fluid flow communication between said channels and said lumen is provided.

* * * * *